United States Patent
Miller, Jr. et al.

(10) Patent No.: US 6,504,051 B1
(45) Date of Patent: Jan. 7, 2003

(54) PROCESS FOR PRODUCTION OF AROMATIC CARBOXYLIC ACIDS WITH IMPROVED WATER REMOVAL TECHNIQUE

(75) Inventors: Harold David Miller, Jr., Kingsport, TN (US); Robert Lin, Kingsport, TN (US); Marcel de Vreede, Poortugaal (NL)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/873,723

(22) Filed: Jun. 4, 2001

(51) Int. Cl.$^7$ .............................................. C07C 51/255
(52) U.S. Cl. .................. 562/409; 562/404; 562/412; 562/413
(58) Field of Search ................. 562/408, 409; 60/685

(56) References Cited

U.S. PATENT DOCUMENTS

| | | |
|---|---|---|
| 4,914,230 A | 4/1990 | Abrams et al. |
| 5,463,113 A | 10/1995 | Yamamoto et al. |
| 5,510,521 A | 4/1996 | McGehee et al. |
| 5,723,656 A | 3/1998 | Abrams |
| 6,137,001 A | 10/2000 | Broeker et al. |

FOREIGN PATENT DOCUMENTS

| | | | |
|---|---|---|---|
| EP | 0 962 442 | * | 12/1999 |
| GB | 1 373 230 | | 11/1974 |
| JP | 55-99517 | | 7/1980 |
| WO | WO 97/27168 | * | 7/1997 |
| WO | WO 98/45239 A1 | | 10/1998 |

OTHER PUBLICATIONS

J. Reumers, Energy Conservation at Amoco Chemicals, Journal A, vol. 25, No. 3, 1984, pp 165–167.
PCT International Search Report (Sep. 9, 2002).

* cited by examiner

Primary Examiner—John M. Ford
Assistant Examiner—Zachary C. Tucker
(74) Attorney, Agent, or Firm—Bernard J. Graves, Jr.; Karen A. Harding

(57) ABSTRACT

Disclosed is an improved process for the continuous production of aromatic carboxylic acids by the liquid-phase oxidation of an alkyl aromatic compound with an oxygen-containing gas in the presence of oxidation catalyst which results in reduced wastewater generation, reduced condensing capacity requirements, and, optionally, increased power recovery, and. The process effectively utilizes the heat of reaction in the process of removing excess water generated from the reaction and minimizes the loss of solvent used as the carrier for the reaction catalyst by removing reactor off-gas directly into a water removal column for distillation. A portion of the overhead aqueous vapors are removed from the top of the water removal column as a vapor distillate, with the remaining overhead aqueous vapors being condensed then subsequently refluxed to the fractionating zone of the water removal column. In a preferred embodiment, the combined vapor distillate and oxygen-depleted process gas are reduced to a low pressure through a power recovery device for improved process efficiency, and then fed to a pollution control device for the destruction of organic compounds before exiting the process.

12 Claims, 3 Drawing Sheets

PROCESS FOR PRODUCTION OF AROMATIC CARBOXYLIC ACIDS WITH IMPROVED WATER REMOVAL TECHNIQUE

FIELD OF THE INVENTION

This invention pertains to an improved process for the continuous production of aromatic carboxylic acids by the liquid-phase oxidation of alkyl aromatic hydrocarbons with molecular oxygen in the presence of an oxidation catalyst or catalyst system wherein an off-gas derived from the oxidation vessel comprising mainly water vapor and minor amounts of organic components is treated in a pollution control device and the aqueous effluent from the pollution control device is removed from the production system. More particularly, this invention pertains to such oxidation processes carried out in a columnar oxidation reactor provided with means to effectively remove water generated by the process with minimal solvent loss utilizing the energy of oxidation wherein the gaseous effluent stream from the water removal means is fed to a pollution control device and the aqueous effluent from the pollution control device is removed from the production system.

BACKGROUND OF THE INVENTION

The liquid-phase oxidation of an alkyl aromatic hydrocarbon to an aromatic carboxylic acid is a highly exothermic reaction commonly carried out in a vented, intimately-mixed, columnar oxidation reactor. The oxidation process comprises continuously feeding, separately or in admixture, an alkyl aromatic hydrocarbon, fresh and/or recycled solvent or reaction medium, and catalyst components to the reactor to which a molecular oxygen-containing gas also is fed, normally at or near the bottom of the reactor. This process gas rises through the liquid contents of the reactor resulting in vigorous agitation of the reaction mixture and providing intimate contact between the alkyl aromatic hydrocarbon and the process solvent having dissolved therein the catalyst or catalyst components. The aromatic carboxylic acid produced is removed continuously through a lower exit port located at or near the base of the reactor as a solid in the solvent which also contains soluble catalyst components. After separation of the aromatic carboxylic acid product, the solvent is returned to the reactor.

Oxygen-depleted process gas along with a minor amount of solvent decomposition products, is removed through an upper exit port located at or near the top of the reactor. The heat of reaction also is removed through the upper exit port by vaporization of process solvent and water generated by the reaction. The oxygen-depleted process gas and the vaporized process solvent and water comprise the reactor off-gas which is typically condensed by means of one or more condensers to separate the solvent and water for recycling to the reactor. The condensed aqueous solvent may be subjected to a water removal step prior to recycling.

The described production system can be utilized in the manufacture of aromatic carboxylic acids at excellent production rates relative to the volume of the reactor. It is necessary that the production system include a means for the efficient removal of the excess water generated by the reaction since the water concentration must be held at an acceptable level, normally between about 3 and 20 weight percent, preferably between about 3 and 10 weight percent, for the reaction to continue at a reasonable rate. The reaction produces one mole of water per mole of carboxyl moiety produced. In addition, there are other by-product reactions that release water, i.e. the direct oxidation of the alkyl aromatic or direct oxidation of the solvent, and water may be added to the process for other reasons such as scrubbing off-gas for solvent recovery. Typically, water is removed by conventional distillation methods.

Direct distillation of the reactor off-gas to remove water has conventionally been employed utilizing the heat of reaction, as described in British Patent Specification 1,373,230 (Yokota et al.) and U.S. Pat. No. 4,914,230 (Abrams et al.), U.S. Pat. No. 5,723,656 (Abrams), and U.S. Pat. No. 5,463,113 (Yamamoto et al.) However, process limitations exist. Since the amount of distillate reflux determines the purity of the overhead distillate and the heat input to the distillation process determines the amount of reflux that the process can accommodate, the heat of reaction fixes both the amount of reflux and the purity of the overhead distillate. The heat of reaction alone is generally insufficient to obtain a desirable overhead purity that minimizes solvent loss. Therefore, direct distillation generally requires additional heat input. U.S. Pat. No. 5,510,521 (McGehee et al.) discloses an improved process wherein oxidation reactor off-gas is fed directly to the lower section of a removal column. A bottoms liquid of partially de-watered process solvent obtained from the lower section of the water removal column is returned to the upper section of the reactor, usually as a spray above the phase separation of the gas/liquid contents of the reactor. The spray of dewatered process solvent enriches the water content of the reactor off-gas to improve the efficiency of the water removal column without additional heat input beyond that of the heat of reaction.

A problem with the removal of water as liquid using direct distillation is that any such water also contains minor amounts of solvent organic by-products, requiring that the stream be treated as wastewater for removal of solvent and organic by-products due to the aforementioned oxidation reactions before release to the environment. The processes described by Yokota et al., McGehee et al., Abrams et al., Abrams, and Yamamoto et al. all remove water as liquid and thus require wastewater treatment for removal of solvent.

Thus, a need exists for a method to remove water from a carboxylic acid production process by a means which does not require wastewater treatment for removal of solvent and organic by-products before release to the environment. Providing such a water removal means would be especially advantageous if it improved process efficiency by recovering additional power using a power recovery device on oxygen-depleted process gas and water vapor streams.

BRIEF SUMMARY OF THE INVENTION

The present invention provides for the removal and treatment of water of reaction as a vapor in a pollution control device, decreasing or eliminating the need for wastewater treatment of the stream for removal of solvent and organic by-products before release to the environment. These and other advantages are afforded by carrying out the oxidation of an alkyl aromatic hydrocarbon in a columnar reactor wherein the reactor off-gas is fed directly into a water removal column. A portion of the overhead aqueous vapors from the water removal column is removed from the top of the water removal column as a vapor distillate, with the remaining overhead aqueous vapors being refluxed to the fractionating zone of the water removal column. The combined vapor distillate and oxygen-depleted process gas are fed to a pollution control device for the destruction of solvent and organic by-products before exiting the process.

Feeding a portion of the overhead aqueous vapor from the water column directly to the pollution control device reduces the required cooling utility duty and required heat transfer area to condense the water from all of the aqueous vapor stream removed from the water column.

Our invention thus provides a process for the continuous production of an aromatic carboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxylic acid solvent which comprises the steps of:

(1) continuously feeding to a reactor alkyl aromatic hydrocarbon, aqueous, monocarboxylic acid solvent having oxidation catalyst dissolved therein, and an oxygen containing gas;

(2) continuously removing from the lower portion of the reactor product-containing liquid comprising aromatic polycarboxylic acid and the aqueous, monocarboxylic acid solvent having the oxidation catalyst dissolved therein;

(3) continuously removing from the upper portion of the reactor and feeding directly into the lower portion of a water removal column reactor off-gas comprising oxygen-depleted process gas and vaporized aqueous, mono-carboxylic acid solvent;

(4) continuously removing from the lower portion of the water removal column a bottoms liquid containing partially de-watered monocarboxylic acid solvent and returning to the reactor at least a portion of the bottoms liquid to the upper section of the reactor;

(5) continuously removing from the water removal column overhead a vapor stream comprised of oxygen-depleted process offgas, water and minor amounts of monocarboxylic acid solvent and organic by-products produced in the oxidation reactor;

(6) feeding a portion of the vapor stream of step (5) to a condenser to obtain (a) a vapor comprising oxygen-depleted process gas and (b) a liquid;

(7) feeding the liquid of step (6)(b) to the fractionating zone of the water removal column; and (8) feeding (i) the remaining portion of the vapor stream of step (5) and (ii) the vapor of step (6)(a), to a pollution control device wherein the monocarboxylic acid and organic by-products present in vapor streams (i) and (ii) are destroyed to obtain an oxygen-depleted process offgas and aqueous vapor stream free or substantially free of organic compounds.

The oxygen-depleted process offgas and aqueous vapor stream free or substantially free of organic compounds obtained from step (8) may be, and normally is, removed from the aromatic carboxylic acid production system. Removal of the water of reaction from the process as a vapor in accordance with step (8) of our novel process avoids the necessity for wastewater treatment of the water of reaction for removal of solvent and organic by-products and reduces the required cooling utility duty and required heat transfer area to condense the water from all of the aqueous vapor stream removed from the water column.

A second and preferred embodiment of the present invention includes the recovery of power from high pressure vapor streams of step (5) and step (6)(a) by feeding those streams to a power recovery device. Thus, this second embodiment provides a process for the continuous production of an aromatic carboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxylic acid solvent which comprises steps (1) through (7) described above in combination with the steps of:

(8.1) feeding (i) the remaining portion of the vapor stream of step (5) and (ii) the vapor of step (6)(a), to a power recovery device wherein the pressure of vapor streams (i) and (ii) is reduced and power is recovered resulting in power recovery and an effluent stream of reduced pressure; and (8.2) feeding the effluent stream of step (8.1) to a pollution control device wherein the monocarboxylic acid and organic by-products present in the effluent stream of step (8.1) are destroyed to obtain an oxygen-depleted process offgas and aqueous vapor stream free, or substantially free, of organic compounds.

The second embodiment of our invention provides the additional advantage of increased power recovery in the process since the water generated in the pollution control devices, e.g., an oxidation reactor, which manifests itself in the form of additional aqueous vapor, is fed to a power recovery device.

A third and further preferred embodiment of the present invention includes preheating the high pressure vapor streams of step (5) and step (6)(a) prior to feeding those streams to a power recovery device. This third embodiment provides a process for the continuous production of an aromatic carboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxylic acid solvent which comprises steps (1) through (7) described above in combination with the steps of:

(8.3) feeding (i) the remaining portion of the vapor stream of step (5) and (ii) the vapor of step (6)(a), to a preheater to increase the temperature of vapor feeds (i) and (ii) by at least 200° C. to obtain a preheater vapor effluent:

(8.4) feeding the preheater vapor effluent from step (8.3) to a power recovery device wherein the pressure of the preheater vapor effluent is reduced and power is recovered resulting in power recovery and an effluent stream of reduced pressure; and (8.5) feeding the effluent stream of step (8.4) to a pollution control device wherein the monocarboxylic acid and organic by-products present in the effluent stream of step (8.4) are destroyed to obtain an oxygen-depleted process offgas and aqueous vapor stream free, or substantially free, of organic compounds.

The third embodiment of the present process preferably utilizes a catalytic oxidation reactor as the pollution control device and the heat produced by the exothermic, oxidative decomposition of organic material in the oxidation reactor is utilized to provide the heat for the preheater. This preferred operation of the third embodiment utilizes the steps of:

(8.3) feeding (i) the remaining portion of the vapor stream of step (5) and (ii) the vapor of step (6)(a), to a preheater to increase the temperature of vapor feeds (i) and (ii) by at least 200° C. to obtain a preheater vapor effluent:

(8.4) feeding the preheater vapor effluent from step (8.3) to a power recovery device wherein the pressure of the preheater vapor effluent is reduced and power is recovered resulting in power recovery and an effluent stream of reduced pressure;

(8.6) feeding the effluent stream of step (8.4) to an oxidation reactor wherein the monocarboxylic acid and organic by-products present in the effluent stream of step (8.4) are removed by exothermic, oxidative decomposition to produce a heated, oxygen-depleted process offgas and aqueous vapor stream free, or substantially free, of organic compounds; and (8.7) feeding the heated, oxygen-depleted process offgas and aqueous vapor stream of step (8.6) to the preheater of step (8.3) to provide the heat required for the operation of the preheater.

The preferred operation of the third embodiment provides the following additional advantages: (1) increased power recovery due to the recovery of heat produced by the exothermic decomposition of organic materials in the catalytic oxidation reactor used as the pollution control device and (2) improved operability due to superheating of the feed to the power recovery device which avoids or reduces the likelihood of vapor condensation in the power recovery device and the mechanical and corrosion problems which may result from such condensation.

BRIEF DESCRIPTION OF THE DRAWINGS

The accompanying

FIG. 1 illustrates a system which does not utilize either a power recovery device or a process preheater.

FIG. 2 illustrates a system which utilizes a power recovery device and corresponds to the second embodiment of the invention described above.

FIG. 3 illustrates a system which utilizes both a process preheater and a power recovery device and corresponds to the above-described third embodiment of the present invention.

The present disclosure is to be considered as an exemplification of the invention without limitation to the specific embodiment illustrated.

DETAILED DESCRIPTION

Figure 1:
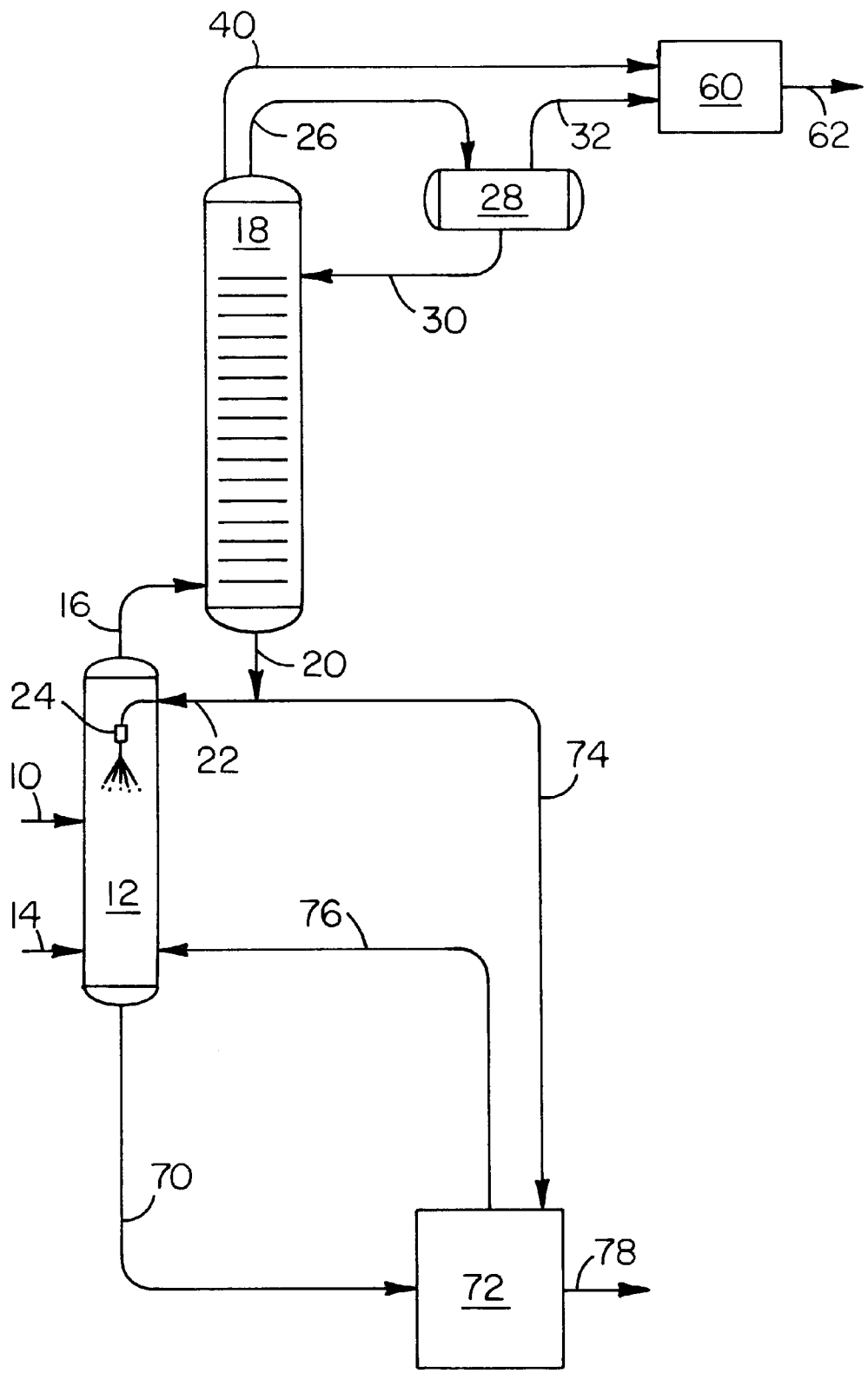
FIGS. 1, 2 and 3 are process flow diagrams illustrating a system embodying the principles of the present invention. While the invention is susceptible to embodiment in various forms, there is shown in the accompanying Figures and hereinafter described in detail a preferred embodiment of the invention.

Referring to the accompanying FIG. 1, reactor feed mixture is introduced via conduit 10 into oxidation reactor 12. The reactor feed mixture comprises an alkyl aromatic hydrocarbon, an aqueous, $C_2$ to $C_6$ monocarboxylic aliphatic acid solvent, and a suitable oxidation catalyst that is typically dissolved in the solvent. The aliphatic, carboxylic acid solvent feed typically contains up to about 10 weight percent water. If desired, the alkyl aromatic compound, and/or aliphatic acid solvent containing catalyst components may be fed to reactor 12 at a plurality of points along the side of the reactor. An oxygen-containing gas under pressure is introduced near the bottom of the reactor 12 via conduit 14. The preferred oxygen-containing gas is air or oxygen-enriched air. The flow rate of the oxygen-containing gas to reactor 12 is controlled to maintain between about 2 and 9 volume percent oxygen (calculated on a dry, solvent free basis) in the off-gas which exits the reactor via conduit 16. The reactants in reactor 12 are maintained at an elevated pressure sufficient to maintain a contained, volatilizable reaction medium substantially in the liquid state at the reaction temperature.

Reactor 12 is a columnar, pressurized, oxidation vessel wherein liquid-phase, exothermic oxidation of the alkyl aromatic hydrocarbon by the oxygen-containing gas takes place in the presence of the oxidation catalyst. The reaction medium contained by reactor 12 thus comprises the oxygen-containing gas, the alkyl aromatic hydrocarbon that is to be oxidized to an aromatic carboxylic acid product, the catalyst, and the aqueous, $C_2$ to $C_6$ monocarboxylic aliphatic acid solvent. Utilizing the method of the present invention, the amount of water within the reactor preferably is between about 3–20 weight percent, most preferably between 3–10 weight percent based on the weight of the water and the aliphatic, carboxylic acid. The temperature and pressure within reactor typically is about 120 to 180° C., preferably about 140 to 160° C. for the oxidation of a xylene to a benzene-dicarboxylic acid, and about 3.5 to 12.1 bar absolute (bara) (50 to 175 pounds per square inch absolute—psia), preferably about 5.5 to 8.0 bara (80 to 110 psia).

During the course of the oxidation reaction, exothermic heat of reaction and water generated by the oxidation of the alkyl aromatic compound are removed from reactor 12 by vaporization of a portion of the liquid reaction medium. These vapors, known as reactor off-gas, comprise the aqueous solvent comprising about 5 to 30 weight percent water and oxygen-depleted process gas containing minor amounts of decomposition products including catalyst residue. The reactor off-gas passes upwardly through the reactor 12 and is conveyed via conduit 16 to the lower portion of water removal column 18 for distillation. The water removal column may be a distillation column having a fractionating zone of either a plurality of trays or a suitable packing for effecting mass transfer and may have twenty-five (25) or more equilibrium stages and a refluxed top section. Normally, all of the heat required to operate distillation column 18 is provided by the reactor off-gas. The pressure within the water removal column typically is about 3 to 11.5 bara (43.5 to 165 psia), preferably about 5 to 7.5 bara (72.5 to 109 psia).

A distilled bottoms liquid containing partially dewatered monocarboxylic aliphatic acid solvent, e.g., monocarboxylic aliphatic acid solvent containing about 4 to 12 weight percent water, is removed from the lower section of water removal column 18 via conduit 20. All or a portion of the partially de-watered solvent is recycled directly to reactor 12 via conduits 20 and 22. The amount recycled directly to reactor 12 ranges from about 10 to 100 weight percent, depending on the amount of partially de-watered solvent utilized for washing catalyst from a product-containing liquid of the reactor 12 as described below. The partially de-watered solvent may be fed at any point to reactor 12. The partially de-watered solvent preferably is fed by means of spray head 24 located below exit conduit 16 and above the phase separation of the gas/liquid contents of reactor 12. Spray head 24 is designed to distribute the partially de-watered solvent in a finely divided form, e.g., droplets, over a substantial portion, preferably over all, of the surface of the phase separation of the gas/liquid reaction mixture. The particular means employed to feed the partially de-watered solvent in the form of a spray to the reactor is not critical so long as it provides liquid-gas contact at the top of the reactor. Thus, the spray may be created by means of a single spray head as shown in FIG. 1 or by a plurality of spray nozzles.

An aqueous vapor stream having minimal monocarboxylic acid solvent therein is removed continuously from the upper section or top of water column 18. This vapor stream typically comprises about 35 to 55 weight percent water, about 1 to 6 weight percent monocarboxylic aliphatic acid solvent and about 42 to 62 weight percent oxygen-depleted process gas. As is shown in the FIG. 1, a portion of the aqueous vapor stream may be removed from water column 18 via conduit 26 and conveyed to condenser 28. The composition of the condensable components (reflux) of the aqueous vapors collected in the condenser 28 preferably is greater than 97 weight percent, most preferably greater than 99 weight percent, water. The reflux is returned to the fractionating zone of the water removal column 18 via conduit 30. The reflux ratio by weight ranges from about 4 to 10 parts reflux to one part aqueous vapor stream. An additional stream of water (not shown) containing minor amounts of acid solvent generated from other water processes such as pump seals, vent scrubbers and water washing may be fed to the water removal column 18. The uncondensed, oxygen-depleted process gas is vented from condenser 28 through conduit 32.

In accordance with the present invention, a second portion, i.e., the remainder, of the oxygen-depleted process offgas and aqueous vapor stream removed from the upper section or top of water column 18 is conveyed to a pollution control device. As is shown in the FIG. 1, a second portion of the aqueous vapor stream may be removed from water column 18 via conduit 40 and conveyed to pollution control device 60. In order to provide a reliable means of controlling the flow of aqueous vapor through conduits 26 and 40, sufficient pressure drop, e.g., from about 0.1 to 1.4 bar (2–20 pounds per square inch—psi) must be provided between the upper portion of the water removal column 18 and the pollution control device 60. This may be accomplished through the use of control valves (not shown) in conduits 32 and 40.

Oxygen-depleted process offgas and aqueous vapor is conveyed via line 40 and uncondensed, oxygen-depleted process gas is conveyed via line 32 to pollution control device 60 wherein the monocarboxylic acid and organic by-products present in streams of conduits 32 and 40 are destroyed to produce an oxygen-depleted process offgas and aqueous vapor effluent stream which is removed from pollution control device 60 via conduit 62. The vapor stream of conduit 62 is free, or substantially free, of organic by-product compounds. The pollution control device may be a flare, a regenerative thermal oxidation unit, an adsorption device such as one or more carbon beds, or a catalytic oxidation unit. Pollution control device 60 preferably is a catalytic oxidation reactor wherein the gas supplied to oxidizer 60 is subjected to a catalytic reaction to oxidize completely small or trace amounts of organic components, e.g., methyl bromide, acetic acid, methyl acetate, para-xylene, carbon monoxide and other by-products produced in oxidizer 12, present in the gas. The oxidizer contains an oxidation catalyst such as noble metal, e.g., platinum and palladium, deposited on a catalyst support material. Such catalytic oxidation units and the operation thereof are well-known to those skilled in the art as shown by Kokai Sho JP 55-99517 and U.S. Pat. No. 5,723,656 referred to previously.

In operation, reactor 12 continuously produces an aromatic carboxylic acid product that is continuously withdrawn as a slurry in the aqueous, monocarboxylic aliphatic acid solvent, which also contains dissolved catalyst. The product-containing liquid is removed from the base of reactor 12 and is conveyed via conduit 70 to a suitable solid/liquid separation zone 72. A portion of the partially de-watered solvent provided by the water removal column may be conveyed via lines 20 and 74 to separation zone 72 for washing catalyst from the product or product-containing liquid. The liquid phase recovered from separation zone 72 comprising aqueous, monocarboxylic aliphatic acid solvent containing dissolved catalyst components is recycled to the lower section of reactor 12 via conduit 76. The solids phase contains the product of the process, aromatic carboxylic acid compound, and is removed from separation zone 72 by means of conduit 78.

Examples of suitable alkyl aromatic hydrocarbons useful as reactor feed-mixture components or ingredients in the process of the present invention and their respective aromatic carboxylic acid products include:

| Aromatic Hydrocarbon | Carboxylic Acid |
|---|---|
| Toluene | Benzoic Acid |
| o-Xylene | Orthophthalic Acid |
| m-Xylene | Isophthalic Acid (IPA) |
| p-Xylene | Terephthalic Acid (TPA) |
| 1,2,3-Trimethylbenzene | Hemimellitic Acid |
| 1,2,4-Trimethylbenzene | Trimellitic Acid |
| 1,2,5-Trimethylbenzene | Trimesic Acid |
| 2,6- and 2,7-Dimethyl-naphthalene | 2,6- and 2,7-Naphthalene-dicarboxylic Acid |

Our novel process is particularly well suited for the production of IPA, trimellitic acid, trimesic acid, the naphthalenedicarboxylic acids, and, especially, TPA which is produced throughout the world in substantial quantities for use in the manufacture of polyesters such as poly(ethylene terephthalate).

Suitable aqueous aliphatic acid solvents useful in the process of our invention are those that are readily volatilizable at the reaction temperatures. Among such solvents are aqueous, aliphatic $C_2$ to $C_6$ mono-carboxylic acids, e.g., acetic acid, propionic acid, n-butyric acid, isobutyric acid, n-valeric acid, trimethylacetic acid, caproic acid, and mixtures thereof. Preferably, the volatilizable monocarboxylic aliphatic acid solvent is acetic acid.

The catalyst systems that may be employed in the oxidation process include any catalyst system conventionally used for liquid-phase oxidation of an alkyl aromatic hydrocarbon. A suitable catalyst system may include a mixture of cobalt, manganese and bromine compounds or complexes, soluble in the particular volatilizable aqueous solvent employed.

Figure 2:
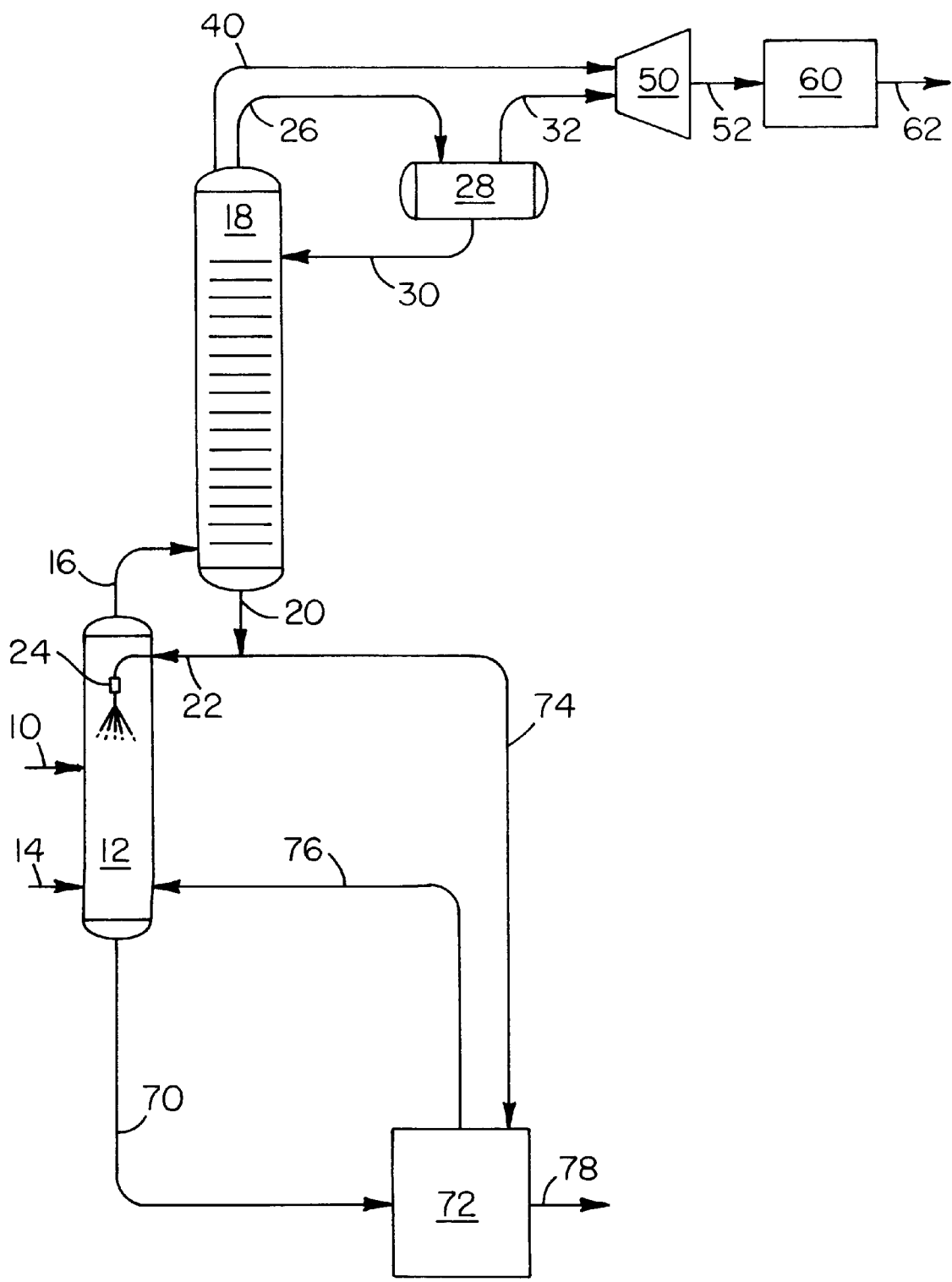

In the second and preferred embodiment of our invention illustrated in FIG. 2, oxygen-depleted process offgas and aqueous vapor is conveyed via line 40 and uncondensed, oxygen-depleted process gas is conveyed via line 32 to power recovery device 50, where power is generated through the reduction of the stream pressures and the associated vapor expansion. The expanded gas exits power recovery device 50 through conduit 52 and is fed to pollution control device 60 wherein solvent and organic by-products are destroyed before the stream exits to the environment through conduit 62. The power recovery device may be any device typically employed to recover power or energy from high-pressure, high-temperature streams in chemical manufacturing processes. See, for example, the devices described in Japanese Patent Application Publication Kokai Sho JP 55-99517, U.S. Pat. No. 5,723,656 and J. Reumers, Energy Conservation at Amoco Chemicals, Journal A, Vol. 25, No. 3 1984, pages 165–167. The power recovery device preferably is a gas turbine or expander.

Figure 3:
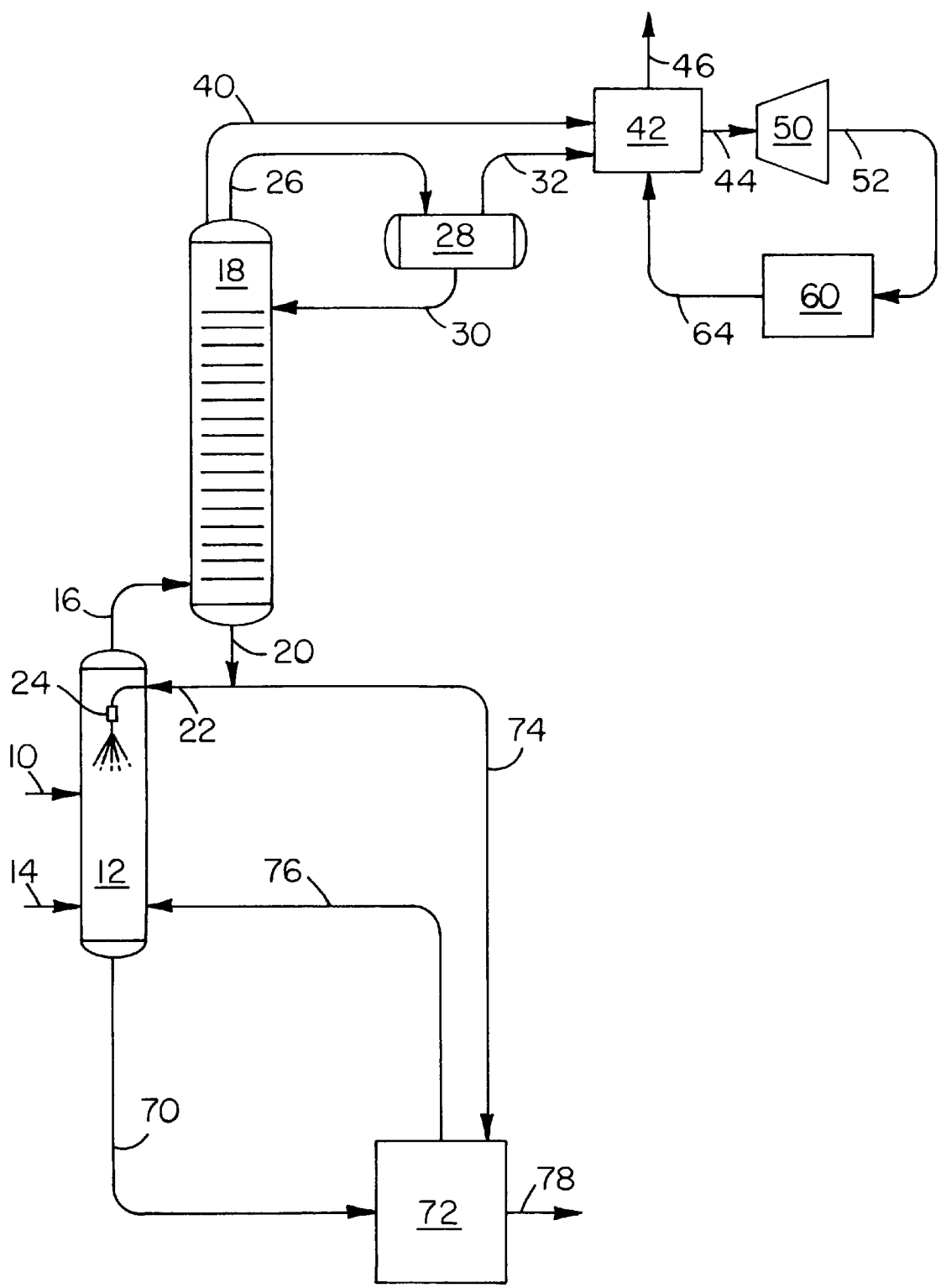

FIG. 3 illustrates the third embodiment of our invention wherein oxygen-depleted process offgas and aqueous vapor are conveyed via line 40 and uncondensed, oxygen-depleted process gas is conveyed via line 32 to preheater 42 wherein the vapor of high pressure streams 32 and 40 is heated to a temperature of at least 300° C., preferably in the range of about 330 to 400° C. As noted above, the preheater avoids or minimizes mechanical and corrosion problems which may occur if vapor condenses in the power recovery device. The heated vapor exits preheater 42 via conduit 44 and is fed to power recovery device 50 wherein the pressure of the preheater vapor effluent is reduced and power is recovered as described above. The preheater ensures that the temperature of the stream exiting the power recovery device is at least 225° C. and preferably in the range of about 255 to 345° C.

As shown in FIG. 3 and described above, the vapor effluent from power recovery device 50 is fed via conduit 52 to pollution control device 60 wherein monocarboxylic acid and organic by-products present in the effluent stream 52 are destroyed to obtain an oxygen-depleted process offgas and aqueous vapor stream free, or substantially free, of organic compounds. The third embodiment of the present process preferably utilizes an oxidation reactor as the pollution control device and the heat produced by the exothermic, oxidative decomposition of organic material in the oxidation reactor provides the heat for preheater 42. This preferred operation of the third embodiment is illustrated in FIG. 3 wherein a heated, aqueous vapor stream free, or substantially free, of organic compounds is transferred by conduit 62 from oxidation reactor 60 to preheater 42 wherein the heat of the vapor of conduit 64 is exchanged with the vapor of high pressure stream 40 an 32. The temperature of the vapor within conduit 64 typically is in the range of about 420 to 480° C. Heat exchanged vapor and gas is removed from preheater 42 via conduit 46 and may be released to the environment.

EXAMPLE

The process provided by the present invention as illustrated by FIG. 3 is further illustrated by the following example. All parts and percentages given in the example are by weight unless specified otherwise. Aqueous acetic acid containing dissolved catalyst was fed at the rate of about 30 parts per hour and p-xylene was fed at the rate of about 1000 parts per hour via conduit 10 to reactor 12. The reactor used was a vertical bubble column having a height:diameter ratio of 12:1. Air containing 0.5% water was fed via conduit 14 at a rate of about 4900 parts per hour air. The oxidation reaction medium filled approximately 85% of the volume of the reactor. The temperature of the vigorously mixed reaction medium was about 140 to 160° C. and the pressure was controlled at about 5.9 bara (85 psia).

A reactor off-gas stream comprising oxygen-depleted process gas, acetic acid and water was removed continuously via a port located at the top of the reactor and transported via conduit 16 to the lower portion of the water removal column 18. The water concentration in conduit 16 was about 9.4% based on the weight of condensable components. A bottom liquid consisting of partially de-watered acetic acid with a water concentration of about 6% by weight was removed via conduit 20 from the water removal column 18 at a rate of about 15,800 parts per hour acetic acid. A portion of the partially de-watered solvent was fed to the reactor via conduit 22 and spray head 24 at a rate of about 9000 parts per hour acetic acid. The remainder of the partially de-watered solvent was fed to the separation system 72 via conduit 74.

An aqueous vapor stream comprising water, acetic acid and oxygen-depleted process gas was removed continuously from the upper section of water column 18. A portion of the aqueous vapor stream was conveyed via line 40 to preheater 42 at a rate of about 470 parts per hour. A second portion (and remainder) of the aqueous vapor stream removed from the upper section of column 18 was conveyed via conduit 26 to condenser 28. The condensable liquid components comprising 99.5% by weight water and 0.5% by weight acetic acid exited the condenser 28 through conduit 30 at a rate of about 3200 parts per hour and were refluxed to the water removal column 18. The resulting reflux ratio of the water removal column was about 6.8. The non-condensables exited the condenser 28 via conduit 32 into preheater 42. Heated vapor from preheater 42 was fed to power recovery device 50 was at a rate of about 4100 parts per hour. Control valves were included in conduits 32 and 40 to provide capability to control process pressure in reactor 12 and flow of aqueous vapor through conduit 40 independently. Power is recovered by reducing the pressure of the combined process streams 32 and 40 in power recovery device 50. Typically, a pressure of about 4.5 to 5.5 bara (65 to 80 psia) within conduits 32 and 40 is reduced to about 1.1 to 1.4 bara (15 to 20 psia) in power recovery device 50. The reduced pressure process stream exits the power recovery device through conduit 52 into catalytic oxidation reactor 60, wherein trace organic components are destroyed, i.e., organic components are oxidized to carbon dioxide and water. Following treatment in pollution control device 60, the oxygen-depleted process gas and water vapor are transferred to preheater 42 via conduit 64. The heat of the vapor removed from oxidation reactor 60 provided the heat required in preheater 42. The heat exchanged vapor provided by conduit 64 then is removed from the production system through conduit 46. In this example, power recovery device was a turboexpander connected to a generator.

The process of our invention was evaluated in a commercial facility wherein p-xylene was oxidized to terephthalic acid as described herein. Operation of the process as described in U.S. Pat. No. 5,510,521 (wherein water of reaction is removed as a liquid) was compared with the process disclosed herein (wherein water of reaction removed as vapor distillate). The experiments demonstrated that, when operating at 70% of plant capacity, wastewater generation rate was reduced by 99% and power recovery was increased by 38%, compared to operation with no flow through conduit 40. As a result of these effects, associated utility costs were reduced by 26%. This cost improvement does not reflect the impact of reduced wastewater treatment costs. Furthermore, power recovery results should improve at higher plant rates due to improved power recovery device efficiency under increased load.

The invention has been described in detail with particular reference to preferred embodiments thereof, but it will be understood that variations and modifications can be effected within the spirit and scope of the invention.

We claim:

1. Process for the continuous production of an aromatic carboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxylic acid solvent which comprises the steps of:

(1) continuously feeding to a reactor alkyl aromatic hydrocarbon, aqueous, monocarboxylic acid solvent having oxidation catalyst dissolved therein, and an oxygen containing gas;

(2) continuously removing from the lower portion of the reactor product-containing liquid comprising aromatic polycarboxylic acid and the aqueous, monocarboxylic acid solvent having the oxidation catalyst dissolved therein;

(3) continuously removing from the upper portion of the reactor and feeding directly into the lower portion of a water removal column reactor off-gas comprising oxygen-depleted process gas and vaporized aqueous, mono-carboxylic acid solvent;

(4) continuously removing from the lower portion of the water removal column a bottoms liquid containing partially de-watered monocarboxylic acid solvent and returning to the reactor at least a portion of the bottoms liquid to the upper section of the reactor;

(5) continuously removing from the water removal column overhead a vapor stream comprising oxygen-depleted process offgas, water and minor amounts of monocarboxylic acid solvent and organic by-products produced in the oxidation reactor;

(6) feeding a portion of the vapor stream of step (5) to a condenser to obtain (a) a vapor comprising oxygen-depleted process gas and (b) a liquid;

(7) feeding the liquid of step (6)(b) to the fractionating zone of the water removal column; and (8) feeding (i) the remaining portion of the vapor stream of step (5) and (ii) the vapor of step (6)(a), to a pollution control device wherein the monocarboxylic acid and organic by-products present in vapor streams (i) and (ii) are destroyed removed to obtain an aqueous vapor stream free or substantially free of organic compounds.

2. The process according to claim 1 wherein the monocarboxylic acid solvent is acetic acid, the alkyl aromatic hydrocarbon is p-xylene, and the aromatic polycarboxylic acid is terephthalic acid.

3. The process according to claim 1 wherein the monocarboxylic acid solvent is acetic acid, the alkyl aromatic hydrocarbon is m-xylene, and the aromatic polycarboxylic acid is isophthalic acid.

4. Process for the continuous production of an aromatic carboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxylic acid solvent which comprises the steps of:

(1) continuously feeding to a reactor alkyl aromatic hydrocarbon, aqueous, monocarboxylic acid solvent having oxidation catalyst dissolved therein, and an oxygen containing gas;

(2) continuously removing from the lower portion of the reactor product-containing liquid comprising aromatic polycarboxylic acid and the aqueous, monocarboxylic acid solvent having the oxidation catalyst dissolved therein;

(3) continuously removing from the upper portion of the reactor and feeding directly into the lower portion of a water removal column reactor off-gas comprising oxygen-depleted process gas and vaporized aqueous, mono-carboxylic acid solvent;

(4) continuously removing from the lower portion of the water removal column a bottoms liquid containing partially de-watered monocarboxylic acid solvent and returning to the reactor at least a portion of the bottoms liquid to the upper section of the reactor;

(5) continuously removing from the water removal column overhead a vapor stream comprising oxygen-depleted offgas, water and minor amounts of monocarboxylic acid solvent and organic by-products produced in the oxidation reactor;

(6) feeding a portion of the vapor stream of step (5) to a condenser to obtain (a) a vapor comprising oxygen-depleted process gas and (b) a liquid;

(7) feeding the liquid of step (6)(b) to the fractionating zone of the water removal column;

(8.1) feeding (i) the remaining portion of the vapor stream of step (5) and (ii) the vapor of step (6)(a), to a power recovery device wherein the pressure of vapor streams (i) and (ii) is reduced and power is recovered resulting in power recovery and an effluent stream of reduced pressure; and (8.2) feeding the effluent stream of step (8.1) to a pollution control device wherein the monocarboxylic acid and organic by-products present in the effluent stream of step (8.1) are destroyed to obtain an oxygen-depleted process offgas and aqueous vapor stream free, or substantially free, of organic compounds.

5. The process according to claim 4 wherein the monocarboxylic acid solvent is acetic acid, the alkyl aromatic hydrocarbon is p-xylene, the aromatic polycarboxylic acid is terephthalic acid and in step (8.1) the pressure of (i) the vapor stream of step (5) and (ii) the vapor of step (6)(a) is about 4.5 to 5.5 bara and the pressure of vapor streams (i) and (ii) is reduced in the power recovery device to about 1.01 to 1.4 bara.

6. The process according to claim 5 wherein the power recovery device comprises a turboexpander.

7. Process for the continuous production of an aromatic carboxylic acid in a pressurized oxidation reactor by liquid-phase, exothermic oxidation of an alkyl aromatic hydrocarbon with an oxygen-containing gas in the presence of an oxidation catalyst and aqueous, $C_2$–$C_6$ aliphatic, monocarboxylic acid solvent which comprises the steps of:

(1) continuously feeding to a reactor alkyl aromatic hydrocarbon, aqueous, monocarboxylic acid solvent having oxidation catalyst dissolved therein, and an oxygen containing gas;

(2) continuously removing from the lower portion of the reactor product-containing liquid comprising aromatic polycarboxylic acid and the aqueous, monocarboxylic acid solvent having the oxidation catalyst dissolved therein;

(3) continuously removing from the upper portion of the reactor and feeding directly into the lower portion of a water removal column reactor off-gas comprising oxygen-depleted process gas and vaporized aqueous, mono-carboxylic acid solvent;

(4) continuously removing from the lower portion of the water removal column a bottoms liquid containing partially de-watered monocarboxylic acid solvent and returning to the reactor at least a portion of the bottoms liquid to the upper section of the reactor;

(5) continuously removing from the water removal column overhead a vapor stream comprising oxygen-depleted process offgas, water and minor amounts of monocarboxylic acid solvent and organic by-products produced in the oxidation reactor;

(6) feeding a portion of the vapor stream of step (5) to a condenser to obtain (a) a vapor comprising oxygen-depleted process gas and (b) a liquid;

(7) feeding the liquid of step (6)(b) to the fractionating zone of the water removal column;

(8.3) feeding (i) the remaining portion of the vapor stream of step (5) and (ii) the vapor of step (6)(a), to a preheater to increase the temperature of vapor feeds (i) and (ii) by at least 120° C. to obtain a preheater vapor effluent;

(8.4) feeding the preheater vapor effluent from step (8.3) to a power recovery device wherein the pressure of the preheater vapor effluent is reduced and power is recovered resulting in power recovery and an effluent stream of reduced pressure; and (8.5) feeding the effluent stream of step (8.4) to a pollution control device wherein the monocarboxylic acid and organic by-products present in the effluent stream of step (8.4) are destroyed to obtain an aqueous vapor stream free, or substantially free, of organic compounds.

8. The process according to claim 7 wherein the monocarboxylic acid solvent is acetic acid, the alkyl aromatic hydrocarbon is p-xylene, the aromatic polycarboxylic acid is terephthalic acid and in step (8.4) the pressure of (i) the vapor stream of step (5) and (ii) the vapor of step (6)(a) is about 4.5 to 5.5 bara and the pressure of vapor streams (i) and (ii) is reduced in the power recovery device to about 1.01 to 1.4 bara.

9. The process according to claim 8 wherein the power recovery device comprises a turboexpander.

10. The process according to claim 7 wherein step (8.5) is replaced with the steps of:

(8.6) feeding the effluent stream of step (8.4) to an oxidation reactor wherein the monocarboxylic acid and organic by-products present in the effluent stream of step (8.4) are destroyed by exothermic, oxidative decomposition to produce a heated, aqueous vapor stream free, or substantially free, of organic compounds; and (8.7) feeding the heated, aqueous vapor stream of step (8.6) to the preheater of step (8.3) to provide the heat required for the operation of the preheater.

11. Process for the continuous production of terephthalic acid in a pressurized oxidation reactor by liquid-phase, exothermic oxidation of p-xylene with an oxygen-containing gas in the presence of an oxidation catalyst and aqueous, acetic acid solvent which comprises the steps of:

(1) continuously feeding p-xylene, aqueous acetic acid solvent having oxidation catalyst dissolved therein, and an oxygen containing gas to a reactor maintained at a temperature of about 120 to 180° C. and a pressure of about 3.5 to 12.1 bar;

(2) continuously removing from the lower portion of the reactor product-containing liquid comprising terephthalic acid and the aqueous, acetic acid solvent having the oxidation catalyst dissolved therein;

(3) continuously removing from the upper portion of the reactor and feeding directly into the lower portion of a water removal column maintained at a pressure of about 3 to 11.5 bara, reactor off-gas comprising oxygen-depleted process gas and vaporized aqueous, acetic acid solvent;

(4) continuously removing from the lower portion of the water removal column a bottoms liquid containing partially de-watered acetic acid solvent containing about 4 to 12 weight percent water and returning to the reactor at least a portion of the bottoms liquid to the upper section of the reactor;

(5) continuously removing from the water removal column overhead a vapor stream comprising about 35 to 55 weight percent water, about 1 to 6 weight percent acetic acid and 42 to 62 weight percent oxygen-depleted process gas;

(6) feeding a portion of the vapor stream of step (5) to a condenser to obtain (a) a vapor comprising oxygen-depleted process gas and (b) a liquid;

(7) feeding the liquid of step (6)(b) to the fractionating zone of the water removal column;

(8.1) feeding (i) the remaining portion of the vapor stream of step (5) and (ii) the vapor of step (6)(a), to a power recovery device wherein the pressure of vapor streams (i) and (ii) is reduced and power is recovered resulting in power recovery and an effluent stream of reduced pressure; and (8.2) feeding the effluent stream of step (8.1) to a pollution control device wherein the acetic acid and organic by-products present in the effluent stream of step (8.1) are destroyed to obtain an aqueous vapor stream free, or substantially free, of organic compounds.

12. Process according to claim 11 wherein the reactor of step (1) is maintained at a temperature of about 140 to 160° C. and a pressure of about 5.5 to 8 bar; the water removal column of step (3) is maintained at a pressure of about 5 to 7.5 bara; and step (4) comprises returning to the reactor at least a portion of the bottoms liquid in the form of a spray above the phase separation of the gas/liquid contents of the reactor.

* * * * *